United States Patent [19]

Norris et al.

[11] Patent Number: 5,614,196
[45] Date of Patent: Mar. 25, 1997

[54] ASH EXTRACTABLES FOR DETERING GYPSY MOTH

[75] Inventors: Dale M. Norris; Ingrid Markovic, both of Madison, Wis.

[73] Assignee: Wisconsin Alumni Research Foundation, Madison, Wis.

[21] Appl. No.: 353,750

[22] Filed: Dec. 12, 1994

[51] Int. Cl.$^6$ .................................................. A01N 65/00
[52] U.S. Cl. ............................... 424/195.1; 424/DIG. 10
[58] Field of Search .......................... 424/195.1, DIG. 10

[56] References Cited

PUBLICATIONS

Black–Schaefer, C.L., and R. L. Beckmann, "Foliar Flavonoids and the Determination of Ploidy and Gender in Fraxinus americana and F. pennsylvanica (Oleaceae)," Castanea 54:115–118 (1989).
Bowers, M. D., and G. M. Puttick, "Response of Generalist and Specialist Insects to Qualitative Allelochemical Variation," Journal of Chemical Ecology, 14:319–334 (1988).
Bowers, M. D., and G. M. Puttick, "Iridoid glycosides and Insect Feeding Preferences: Gypsy Moths (Lymantria dispar, Lymantriidae) and buckeyes (Junonia coenia, Nymphalidae)," Ecological Entomology 14:247–256 (1989).
Doskotch, R. W., et al., "Nerolidol: An Antifeeding Sesquiterpene Alcohol for Gypsy Moth Larvae From Melaleuca leucadendron," Journal of Chemical Ecology, 6:845–851 (1980).
El–Naggar, S.F., et al., "Antifeedant Diterpenes for the Gypsy Moth Larvae from Kalmia latifolia: Isolation and Characterization of Ten Grayanoids," Journal of Natural Products, 43:617–631 (1980).
El–Naggar, L.J., and J. L. Beal, "Iridoids. A Review," Journal of Natural Products, 43:649–707 (1980).
El–Naggar, S.F., and R. W. Doskotch, "Specioside: A New Iridoid Glycoside from Catalpa speciosa," Journal of Natural Products, 43:524–526 (1980).
Gianinetto, I.B., et al., "Isolation of N–Methylcassine from Species of the Genus Prosopis," Journal of Natural Products, 43:632–633 (1980).
Inouye, H., et al., "Glucosides of Fraxinus japonica," Phytochemistry, 14:304 (1975).
Inoue, K., et al., "Four Secoiridoid Glucosides from Jasminum Mesnyi," Phytochemistry, 30:1191–1201 (1991).
Kubo, I., et al., "The Structure of Xylomollin, a Secoiridoid Hemiacetal Acetal," Journal of the American Chemical Society, 98:6704–6705 (1976).
Kuwajima, H., et al., "Secoiridoid, Coumarin and Secoiridoid–Coumarin Glucosides from Fraxinus chinensis," Phytochemistry, 31:1277–1280 (1992).
LaLonde, R. T., et al., "Polyglucosidic Metabolites of Oleaceae. The Chain Sequence of Oleoside Aglucon, Tyrosol, and Glucose Units in Three Matabolites from Fraxinus americana," Journal of the American Chemical Society, 98: 3007–3013 (1976).
Meisner, J., and U. Skatulla, "Phagostimulation and Phagodeterrency in the Larva of the Gypsy Moth, Porthetria dispar L.," Phytoparasitica, 3:19–26 (1975).
Mosher, F. H., Food Plants of the Gipsy Moth in America, Bulletin 250, U.S. Dept of Agriculture, pp. 1–39 (1915).
Ngadjui, B.T., et al., "Prenylated Coumarins from the Leaves of Clausena anisata," Journal of Natural Products, 52:243–247 (1989).
Shen, Y.–C., et al., "Secoiridoid Glycosides from Jasminum multiflorum," Phytochemistry, 29:2905–2912 (1990).

Primary Examiner—John W. Rollins
Attorney, Agent, or Firm—Quarles & Brady

[57] ABSTRACT

A method of preparing a substance capable of deterring gypsy moths and gypsy moth larvae is disclosed. Green ash foliage are placed in contact with methanol for a period of time sufficient to extract methanol-soluble compounds from the foliage. The foliage-methanol mixture is filtered, and the filtrate is concentrated. The concentrated filtrate is then contacted with ethyl acetate for a period of time sufficient to extract ethyl acetate-soluble compounds from the concentrated filtrate.

8 Claims, 4 Drawing Sheets

FIG. 1

1T, No-choice feeding by gypsy moth larvae on disk of green ash foliage; 1C, No-choice feeding on disk of a preferred host tree, red oak.
2TC, Choice feeding on ash (left) versus red oak (right).
3TC, Choice feeding on oak plus 40 µl of 5 mg/ml of non-hydrolyzed ethyl acetate extractables from green ash foliage (T, left disk) versus on oak (control) (C, right disk).
4TC, Choice feeding on oak plus 40 µl of 0.1 mg/ml of non-hydrolyzed ethyl acetate extractables from green ash foliage (T, left disk) versus on oak (control) (C, right disk).
5TC, Choice feeding on oak plus 40 µl of 10 mg/ml of the hydrolyzed ethyl acetate extractables from green ash foliage (T, left disk) versus on oak (control) (C, right disk).
6TC, Choice feeding on oak plus 40 µl of the 5 mg/ml of the aqueous ($H_2O$) extractables from green ash foliage (T, left disk) versus oak (control) (C, right disk).

FIG. 2

Choice Test:

T (treatment) - red oak (preferred host) leaf disk plus 40 μl of 15 mg/ml of non-hydrolyzed ethyl acetate green ash extractables dissolved in methanol.

C (solvent control) - red oak leaf disk plus 40 μl of methanol (solvent).

ASH EXTRACTABLES FOR DETERRING GYPSY MOTH

FIELD OF THE INVENTION

The present invention relates to a method of producing a substance capable of deterring gypsy moths and gypsy moth larvae in which ethyl acetate extractables are isolated from the green ash tree. The substance can be applied to plants, shrubs and trees susceptible to gypsy moth attack.

BACKGROUND OF THE INVENTION

The gypsy moth (Lepidoptera: Lymantriidae, *Lymantria dispar L.*) is one of the most feared defoliators of more than three hundred of man's most valued plants, shrubs and trees throughout much of the world. In particular, the gypsy moth attacks oak, aspen, other deciduous trees, and some conifers, causing a significant economic problem throughout the world. Hundreds of millions of dollars have been spent to suppress the damage from this major pest. In addition, the nuisance from large numbers of gypsy moth caterpillars and dropping frass (i.e., feces) severely reduces the aesthetic and recreational values of individual shade trees as well as forests.

Two possible methods to control gypsy moths include injection of systemic insecticides into susceptible plants, and/or application of a bacterial pathogen (*Bacillus thuringiensis* var. Kurstaki) of gypsy moths. Both methods are costly. Systemic insecticide injection into valued trees costs approximately \$6/5 $m^3$ of trunk. Aerial application of the commercially available bacterial pathogen of the insect costs approximately \$5.25–7.00/acre. However, both the systemic insecticide and the bacterium are toxic to other life in the environment, and provide inconsistent suppression of gypsy moth.

There has consequently been a significant effort to develop cost-effective antixenosic and/or antibiotic substances specifically targeted to the gypsy moth, which substances are nontoxic to other life. Antixenosis is a condition which causes an insect to not prefer, or to prefer less, a plant as host, and/or to alter its behavior in ways which decrease its feeding, oviposition and/or sheltering. Antibiosis is a plant condition in which metabolic inhibition and/or toxicity occurs.

In most bioassays testing potential insect repellents and insecticides, duration of the experiment and chemical concentration seem to be major factors in determining whether antixenosis and/or antibiosis will occur. In shorter experiments, antixenosis is more likely; in longer ones the effect is often a combination of antibiosis and antixenosis. Lower concentrations frequently yield antixenosic, but not antibiotic effects.

Researchers have long observed that certain plants repel pestilential insects, including *L. dispar*. For example, it has been observed that leaf extractables of *Pinus silvestris L.* and *Ilex aquifolium L.*, and the specific monoterpenes: α-pinene, β-pinene, 3-carene and camphene have phagodeterrent effects on *L. dispar*. When applied on standardized styrofoam disks, all chemical treatments showed a significant reduction in larval feeding. The researchers hypothesized that leaves of *P. silvestris*, being rich in etheric oils, also may produce volatile deterrents. Meisner, J. and Skatulla, U., *Phytoparasitica* 3: 19–26. (1975).

The antifeedant effects of *Kalmia latifolia L.* leaf extractables have also been tested on *L. dispar* larvae. Ten antifeedant diterpenes were isolated and characterized from the ethyl acetate-extractable fraction of the ethanolic extractables. Kalmitoxin-I, kalmitoxin-IV and grayanotoxin-III were shown to be the more active. The level of activity was determined as dryfrass weight per treatment, and was reported as a percentage of feeding reduction by a treatment as compared to the control (red oak). El-Naggar, S. F., Doskotch, R. W., Odell, T. M., and Girard, L., *J. Nat. Prod.* 43:617–631 (1980).

A sesquiterpene alcohol, nerolidol, isolated from the hexane extractables of the *Melaleuca leucadendron L.* leaf also has been shown to act as a feeding deterrent. Doskotch, R. W., Cheng, H.-Y., ODell, T. M., and Girard, L., *J. Chem. Ecol.* 6:845–851 (1908). Although nerolidol is not considered to be a highly potent compound, its high concentration in the plant may explain its observed activity. Related alcohols such as geraniol (a monoterpenoid alcohol present in the genus Jasminum of the family Oleaceae) and farnesol, showed more activity than nerolidol. In contrast, the simpler isoprene-structured compounds, 2-methyl-3-buten-2-ol and t-amyl alcohol, were inactive. Gibbs, R. D., McGill-Queen's University Press, Montreal (1974).

It has also been found that the feeding deterrency of *Catalpa speciosa* Warder leaf extractables is due to the synergistic effects of several compounds. Fractionation of the active ethyl acetate extractables yielded several inactive, or very weakly active, compounds; two of which were identified as the iridoid glycosides, catalposide and specioside (weakly active). Dry fecal weight was the measure of feeding. El-Naggar, S. F. and Doskotch, R. W., *J. Nat. Prod.* 43: 524–527 (1980).

In 1915, researchers first observed that the green ash tree (*Fraxinus pennsylvanica*, family Oleaceae) had an antibiotic effect on *L. dispar*. Antibiosis was observed when the researchers examined the effects of *F. pennsylvanica* foliage on first- to fourth-instar larvae. Larvae placed on green ash leaves starting in any of the four stadia were unable to pupate. Mosher, F. H., *USDA Technical Bulletin* 250:3–39 (1915).

Later researchers found that second-instar *L. dispar* larvae died when an extract of neem seeds (*Azadirachta indica*), which contains azadirachtin (a known insect antifeedant and antibiotic), was added to an artificial diet. Skatulla, U. and Meisner, J., *Umweltschutz* 48: 38–40 (1975).

Other researchers have tested the effects of terpenoid-based compounds on *L. dispar* growth and survival. For example, when the four biosynthetically related iridoid (cyclopentan-(c)-pyran monoterpenoid) glycosides aucubin, catalpol, loganin and asperuloside, were added to an artificial diet, the researchers observed a significant reduction in larval growth and survival as compared to the control. Bowers, D. M. and Puttick, G. M., *J. Chem. Ecol.* 14: 319–333 1988.

The same researchers later tested the effect of different concentrations of the iridoid glycoside catalposide on the growth rate and the survival of two wild, and one laboratory, strains of larvae. Using much higher doses of catalposide than were used by El-Naggar and Doskotch (as reported in *J. Nat. Prod.* 43: 524–527, 1980), Bowers and Puttick found that one wild strain both grew (based on larval weight) and survived significantly better on the lowest allelochemical concentration. Growth rate and survival of the other two strains were not affected by treatments. Bowers, D. M. and Puttick, G. M., *Ecol. Entomol.* 14: 247–256 (1989).

Terpenoid-based compounds are prevalent in the family Oleaceae, which includes the green ash tree (genus Fraxinus). The potent insect deterrents iridoid glycosides (described above) are abundant in Oleaceae. The Oleaceae iridoid glycosides include syringenone and syringoxide (from genus Syringa and Phyllinea), syringopicroside (from genus Syringa) and forsythide and forsythide methyl ester (from genus Forsythia).

Monoterpenoid alcohols reported in the Oleaceae family include geraniol, d-linalool and 1-α-terpineol (found in genus Jasminum). Triterpenoids include oleanolic acid (from genus Ligustrum and genus Olea), O-acetyl-oleanolic acid (found in genus Ligustrum), squalene (from genus Olea) and ursolic acid (from genus Osmanthus). This family also contains the following tetraterpenoids: antheraxanthin esters, cryptoxanthin-epoxide esters, cryptoxanthin esters, flavoxanthin, lutein esters, neoxanthin esters and violaxanthin (from genus Forsythia), as reported in Gibbs, 1974, cited above. Secoiridoid glucosides found in the Oleaceae family, but not generally in the genus Fraxinus, include 10-hydroxy-ligustroside (from genus Ligustrum), 10-acetoxy-ligustroside and 10-acetoxy-oleuropein (from genus Osmanthus, as reported in El-Naggar and Beal, *J. Nat. Prod.* 3: 649–707, 1980), multifloroside, multiroside and 10-hydroxyoleoside-11- methyl ester (genus Jasminum, as reported in Shen et al., *Phytochem.* 29: 2905–2912, 1990), and 2" hydroxyjasminin, isojasminin, 4"-hydroxyisojasminin and jasmosidic acid (from genus Jasminum, as reported in Inoue et al., *Phytochem.* 30: 1191–1201, 1991).

Secoiridoids are known to be potent antifeedants against some insects. For example, xylomollin, a bitter compound of unripened fruits of *Xylocarpus molluscensis*, showed antifeedant activity against the African army worm. Kubo et al., *J. Am. Chem. Soc.* 98: 6704–6705 (1976). Secoiridoid glucosides specifically found in the genus Fraxinus include oleuropein (as reported in Inouye et al., *Phytochemistry* 14: 304, 1975); ligstroside and nuzhenide (as reported in LaLonde et al., *J. Am. Chem. Soc.* 98: 3007–3013, 1976); and neooleuropein (as reported in Kuwajima et al., *Phytochemistry* 31: 1227–1280, 1992). Kuwajima et al. also reported a new substance, frachinoside (cichoriinylsecoxyloganin), the first secoiridoid glucoside linked to a coumarin glucoside in the Fraxinus genus. LaLonde et al. (1976) also reported bisglycosidic secoiridoids GI-3 and GI-5 from Fraxinus spp.

The chemistry of the genus Fraxinus also includes numerous coumarin glycosides and various aglycones. A glycoside is a compound with a semiacetal linkage between a sugar and an alcoholic or phenolic group, which is called an aglycone. Paris, *Chemical Plant Taxonomy*, T. Swain [ed.]. Academic Press, London, pp. 337–358 (1963).

Coumarin glycosides in the genus Fraxinus include fraxin (as reported in Jensen et al., *The Chemistry of Wood*, B. L. Browning [ed.], John Wiley & Sons, New York, pp. 589–666, 1963; and Paris, 1963), esculin (as reported in Jensen et al., 1963; and Paris, 1963), cichorin (as reported in Harborne and Simmonds, *Biochemistry of Phenolic Compounds*, J. B. Harborne [ed.]. Academic Press, London, pp. 78–127, 1964) and daphnin (as reported in Robinson, The Organic constituents of higher plants. Their Chemistry and Interrelationships, 6th ed. Cordus Press, Massachusetts, 1991).

Coumarin aglycones in Fraxinus include fraxetin and isofraxetin (Harborne and Simmonds, 1964); esculetin (Robinson, 1991); and umbelliferone, scopoletin and xanthoxyletin (Jensen et al., 1963). These aglycones are reported to be strong antifeedants and antibiotics. Ngadjui et al., *J. Nat. Prod.* 52: 243–247 (1989); Su and Horvat, *J. Agric. Food Chem.* 35: 509–511 (1987).

Glycosides of flavonoids in Fraxinus include quercetin 3-O-rutinoside, luteolin 7-O-glucoside, luteolin 7-O-rutinoside, apigenin 7-O-rutinoside and acacetin 7-O-glucoside. The flavonoid aglycones, luteolin and 7-methoxy luteolin, were reported in green ash foliage. Black-Schaefer and Beckmann, Castanea 54: 115–118 (1989).

SUMMARY OF THE INVENTION

The present invention is summarized as a method of preparing a substance capable of deterring gypsy moths and gypsy moth larvae. Green ash foliage is placed in contact with methanol so as to extract methanol-soluble compounds from the foliage. The foliage-methanol mixture is filtered, and the filtrate is concentrated. The concentrated filtrate is then contacted with ethyl acetate so as to extract ethyl acetate-soluble compounds from the concentrated filtrate. The resultant ethyl acetate extract is a gypsy-moth deterring substance which can be applied to susceptible plants to protect them from the ravages of the insect.

It is an object of the present invention to describe a methodology which results in a consistent production of a substance capable of deterring gypsy moths and larvae.

It is another object of the present invention to provide a cost-effective antixenosic and/or antibiotic substance specifically targeted to the gypsy moth and larvae, which substance is nontoxic to other life.

Other objects, advantages, and features of the present invention will become apparent from the following specification.

DETAILED DESCRIPTION OF THE INVENTION

The present invention is directed toward a method of producing a substance capable of deterring gypsy moths and gypsy moth larvae, in which ethyl acetate extractables are isolated from foliage of the green ash tree. The extracts can be applied to plants, shrubs and trees susceptible to gypsy moth attack to deter gypsy moth feeding.

The preferred method in accordance with the present invention contemplates that foliage from the green ash tree (*Fraxinus pennsylvanica*) is collected and contacted with methanol so as to extract, or leach, the methanol-soluble compounds present in the foliage. The foliage-methanol mixture is then filtered. The filtrate is concentrated, and the concentrated filtrate is extracted with ethyl acetate.

A preferred embodiment of the present invention is described as follows. Green ash foliage (including leaves and petioles) are collected and placed in 80% methanol. The preferred ratio of foliage to 80% methanol for storage is in the range of about 0.06–0.13 g foliage/ml methanol. The foliage/methanol mixture is stored in darkness at −20° C. until use.

For further processing of the foliage/methanol mixture, all individual leaflets are removed from each compound ash leaf, and the resultant denuded leaf petioles are cut into sections approximately 0.5 cm long. Preferably, the approximately 100 grams of mixed leaves and petiole sections are combined and homogenized in the storage solvent plus 100 ml of fresh methanol for about 10 min at 50% maximum speed. The resultant homogenate is then filtered under lab-line vacuum. The filtrate, containing methanol extractables, is then reduced in volume by rotoevaporation, preferably at a temperature of approximately 42° C.

The concentrated methanol extractables are then extracted with ethyl acetate, preferably by partitioning three times in a separatory funnel. The resultant three ethyl acetate fractions per methanol sample are combined, rotoevaporated to dryness, and redissolved in a small volume (approximately 5–10 ml) of ethyl acetate. The ethyl acetate extracts are then placed in vials, dried under a stream of nitrogen, and stored in darkness at −20° C. until use as a substance capable of deterring gypsy moths and larvae from susceptible plants.

To use the substance of the present invention, it is preferred to dissolve a known amount of the dried ethyl acetate extract in 100% methanol. The concentration of extract to methanol is expressed in mg extract per ml methanol. The preferred concentration for the substance is about 3 mg/ml; however, the substance is significantly effective both at much lower concentrations (about 0.1 mg/ml), and much higher concentrations (about 15 mg/ml).

The gypsy moth-deterring substance can be topically applied to susceptible plants. In trees, bands of the substance can be placed around the trunk. The female gypsy moth does not fly, and therefore larvae dispersal is important. At the fourth instar stage, the gypsy moth larvae become active at night but seek shelter during the daytime hours at the base of the trunk or in soil litter. Therefore, the movement of the gypsy moth larvae up and down the tree trunk can be disrupted by trunk bands containing anti-gypsy moth extractables. In shrubs and other plants lacking a trunk, the substance can be sprayed or otherwise applied on the stem or on the foliage.

To date, the active compounds in the gypsy moth-deterrent ethyl acetate extractables have only been characterized by high performance liquid chromatograph analysis (HPLC). The chromatogram resulting from this analysis is included as FIG. 1. The gypsy-moth deterring compounds which were extracted from green ash foliage probably include glucosides, phenolics, and terpenoids (secoiridoids). In the chromatograph, a horizontal bracket marked with a star indicates the HPLC peaks of the active ingredients associated with the feeding deterrent activity. Clearly, other separations are possible to separate the active ingredients further, if desired. The peaks of the active ingredients here show retention times of 13.67, 13.96, 14.19, 14.20, 14.46 and 14.82 minutes, which correspond to relative times for passage through the column using the specified solvent-gradient program. Using the exact HPLC conditions specified below, these same peaks can be resolved in other green ash foliage extractables. More definite determinations of the chemical structures of the biologically active compounds from green ash foliage can be carried out using GS-MS and NMR.

EXAMPLES

I. Preparation and Analysis of Experimental Materials

Collection of Leaves from *F. pennsylvanica* and from *Quercus rubra* L. were collected from locations which have not been exposed to aerial and/or other kinds of pesticide application, and which are relatively protected from excessive pollution. Five trees of *F. pennsylvanica* and *Quercus rubra* L., located on the University of Wisconsin, Madison, Wis. campus were selected for insect-feeding and chemical-analyses studies. Eight trees were sampled from a second, suburban Madison location.

Moisture determination Moisture determinations were made on *F. pennsylvanica* leaves. Four leaves were collected from each of the five green ash trees on campus. Fresh weight of the leaves was determined immediately after sampling. Leaves were then put into preweighed weighing bottles, dried in the open bottle in an oven for 24 h at 110° C. and then cooled in a desiccator for about 45 min before reweighing in the resealed bottle. Dry weight of the leaves was determined, and the percent of moisture per leaf was calculated according to the following formula:

$$\% \text{ water} = \frac{\text{fresh leaf weight} - \text{dry leaf weight}}{\text{fresh leaf weight}} \times 100$$

Extraction procedure 50–100 g of green ash foliage were randomly chosen from each tree and placed immediately into a screw-cap glass jar containing 800 ml of 80% methanol. Leaves were then stored in darkness at −20° C. until chemical analysis.

All individual leaflets were removed from each compound ash leaf per jar, and the resultant denuded leaf petioles were cut into 0.5-cm long sections. The petiole sections and individual leaflets per jar were then combined and homogenized in 900 ml of 80°–100% methanol for about 10 min at 50% maximum speed, using an Omni-mixer obtained from Ivan Sorvall, Inc., Norwalk, Conn. The resultant homogenate was then filtered through Whatman No. 2 paper under vacuum. The filtrate was reduced by rotoevaporation at 42°±2° C.

The concentrated methanol extractables resulting from homogenization of 10 g (fresh weight) of leaves were partitioned three times in a separatory funnel with 100-ml ethyl acetate. The three ethyl acetate fractions per methanol sample were combined, rotoevaporated to dryness and then redissolved in 5 to 10-ml ethyl acetate. Each sample was then placed in a preweighed screw-cap vial, dried under a stream of nitrogen and weighed. Samples in screw-capped vials were then wrapped in aluminum foil and stored at −20° C. in darkness.

The remaining aqueous fraction (after ethyl acetate partitioning from the methanol extractables) was transferred into a preweighed screw-cap vial, lyophilized for 36–48 hr and the dry weight was determined. Vials with dry aqueous extractables were then stored at −20° C. in darkness until use.

Insect rearing Gypsy moth egg masses were obtained from the Otis Air Force Base rearing facility in Massachusetts where insects are raised on artificial diet. If egg masses were not immediately used upon arrival they were stored at +10° C. in darkness. Egg masses were sterilized 5 min in the following solution: 40 ml of 5.25% sodium hypochlorite added to 2060 ml of double distilled water containing 40 ml of Tween-80. The solution was agitated for 5 min before use. After sterilization, egg masses were rinsed for 10 min with distilled water and then dried. Thorough drying of egg masses before their introduction into the feeding arena was an important step because it decreases the suitability for fungal development.

Rearing during this study was conducted in a commercial wheat germ-based artificial diet (ICN) in incubators at 25°±1° C. with a photoperiod of 15:9 (L:D). Sterilized individual egg masses was placed in individual plastic dishes (15.5×4.0-cm) and presented with a piece of diet (roughly 1.5×1.0×1.0 cm). Diet was replaced every 2–3 days, or when necessary. Sterile technique were employed throughout the study. This rearing method was established for use in the gypsy moth quarantine facility of the University of Wis., Madison.

High Performance Liquid Chromatographic (HPLC) Analyses A 10-mg aliquot of each sample was dissolved in 1-ml HPLC-grade methanol (Aldrich Chemical Company), vortexed for 1 min and then passed through a Gelman Nylaflo 0.20-µm filter. Just before the injection into the HPLC, each sample was vortexed for 1 min; then a 20-µl volume was injected into a Beckman Ultrasphere ODS 5-u column (4.6 mm×25 cm). The eluting solvent system consisted of 2% acetic acid: acetonitrile (90% : 10%) for 5 min, then a linear gradient to 100% acetonitrile in 25 min, and then back to the starting ratio in 3 min. There were three replicate injections per sample. The HPLC system was controlled by an Altex 422 programming microprocessor and two Altex 100A pumps. The UV detector was set at 254-nm absorbance. Data was integrated and peak areas recorded through a Spectra Physics 4400 computing integrator.

Figure 1:
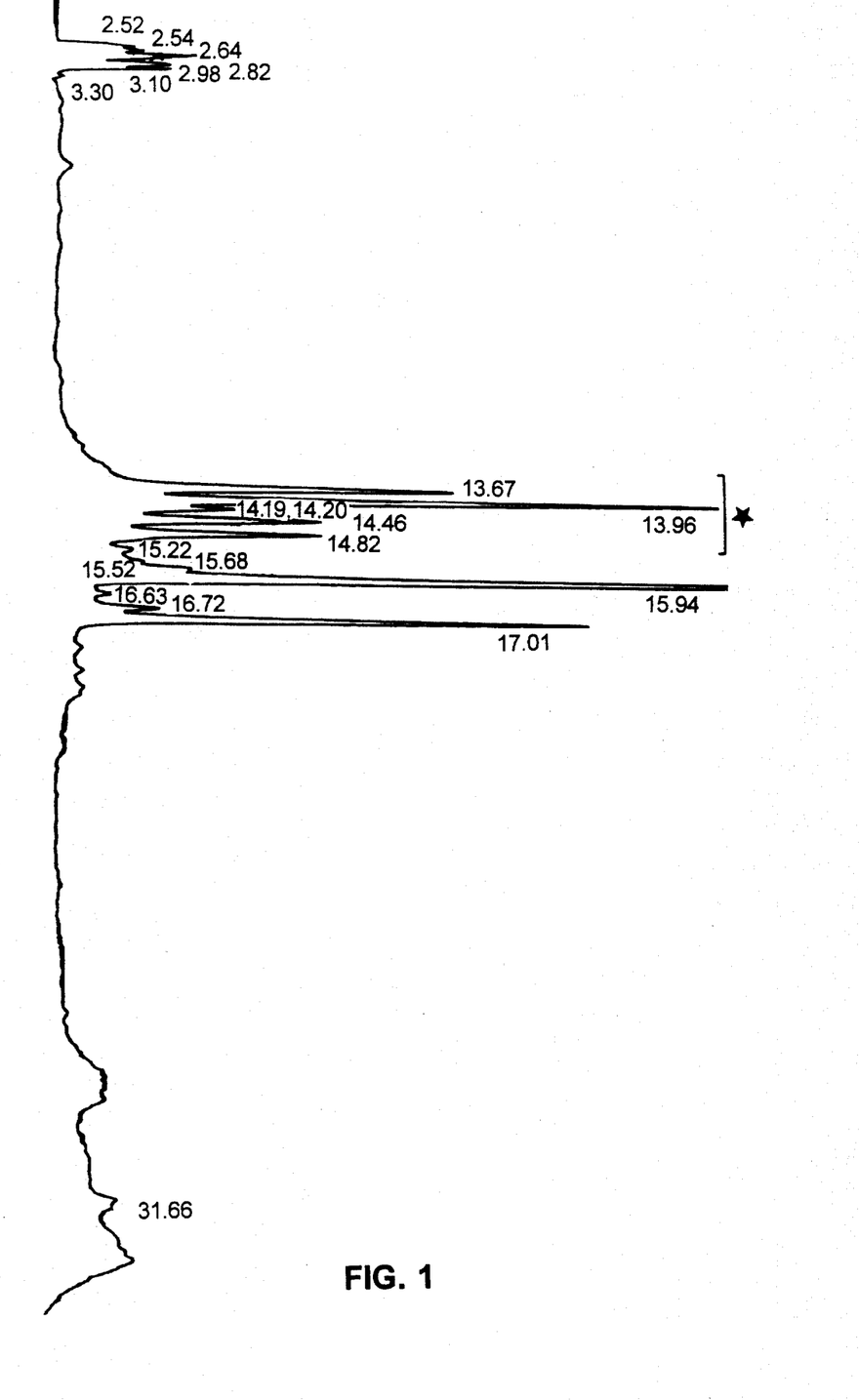
FIG. 1 is a reproduction of a chromatogram resolving the gypsy moth-deterring substances of the present invention.

FIG. 1 is a chromatograph representing the gypsy moth-deterrent extract of the present invention.

II. Experiments Regarding *F. pennsylvanica* Foliage Antixenosis to *L. dispar*

General considerations In all antixenosis experiments, neonates were reared on artificial diet until they reach a certain instar (i.e., usually third) suitable for the feeding bioassay; then larvae were pulled out from other larvae of a given egg mass and placed in groups of twenty in a plastic dish (11.5×4.5-cm) containing a feeding cube. These third-instar larvae were uniformly starved by removing the cube of diet 4.5–5 hr prior to the initiation of the experiment. Transferring larvae from artificial diet to fresh leaf disks did not significantly disrupt their feeding. Larvae from individual egg masses were distributed across various treatments to offset for the maternal and/or genetic variations. An experiment was terminated when 50% of the area of either leaf disk in an arena was removed, or when 17 hr had elapsed.

Preference between red oak and green ash foliage A preference test was employed to determine further the non-host/host status of *F. pennsylvanica* foliage regarding *L. dispar*. Twenty-four-hour-old third-instar larvae were used in feeding bioassays. There were 15 replicates based on 15 egg masses per treatment; two larvae from a given egg mass will constitute a replicate. Gypsy moth larvae were fed with green ash and/or red oak leaf disks cut with a No. 8 (1.5-cm-diam) cork borer. The feeding arena consisted of a plastic dish (9×1.3-cm) with a 2–3-mm thick layer of paraffin on the bottom of the dish. One 9-cm-diam No. 1 filter paper was attached to the inside surface of the lid of each arena and another was attached on the paraffin bottom. The top paper was moistened as necessary to maintain the turgidity of the leaf disks. Two 1.2-cm-long insect pins were used to secure each leaf disk to the paper-covered paraffin bottom of the arena.

Two-choice assay In this choice test, insects had a feeding option between comparable leaf disks from green ash and red oak (a preferred host). Each leaf disk was placed about 1.5 cm from the edge of the arena leaving about 1.5 cm centrally between the two disks in the arena setup. Two larvae were introduced centrally into the feeding arena.

No-choice assay In the no-choice assay, a single larva was offered either a green ash (treatment) or a red oak (preferred control) leaf disk. An adjacent treatment- or control-containing arena was considered as the other member in this paired, but no-choice, assay.

Figure 2:
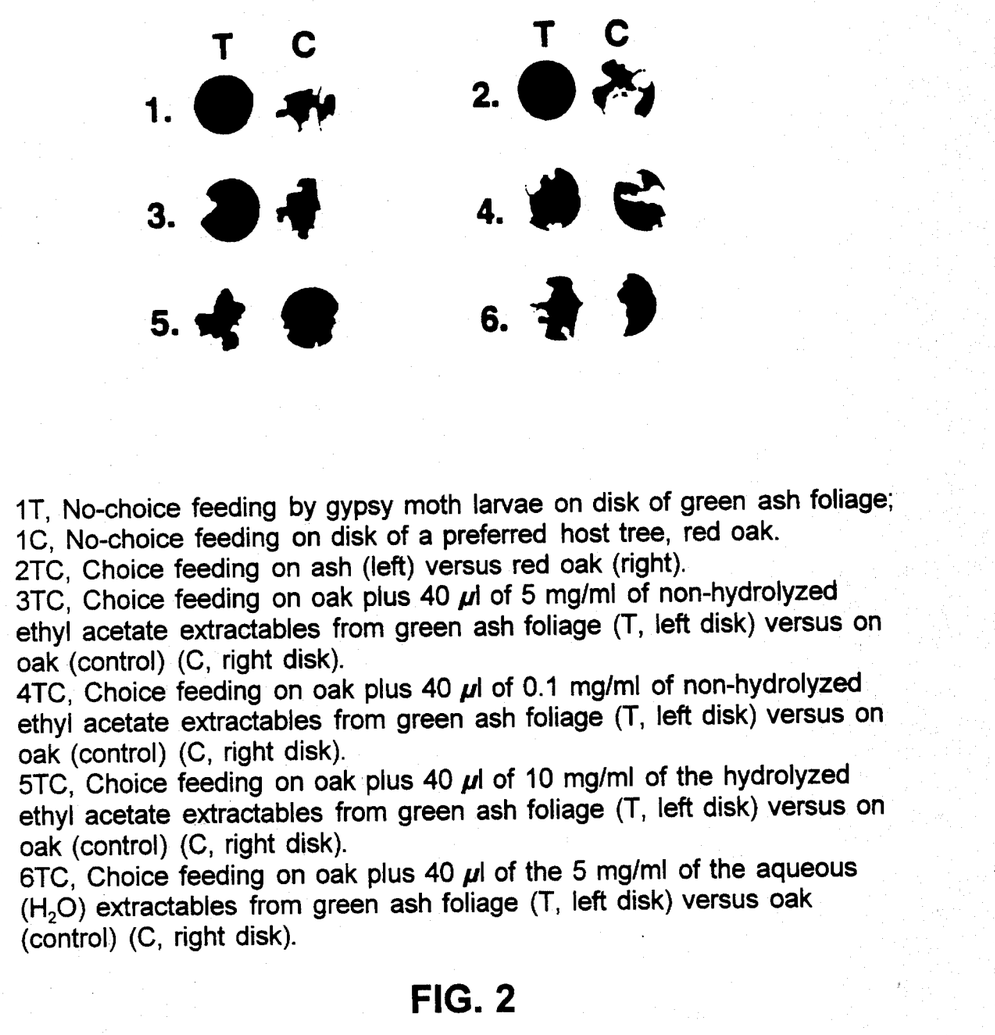
FIG. 2 is a schematic illustration of feeding trial results on two leaf disks; one of which was either non-host green ash or treated red oak, and the other was red oak (preferred host).

The results from the Section II tests are presented in FIG. 2. As is evident from tests 1 and 2, gypsy moth larvae clearly prefer red oak over green ash leaves.

III. Fractionation of green ash ethyl acetate extractables

The fractionation of the ethyl acetate extractables of green ash foliage was conducted to determine what fraction(s) have the biological activity. Ten mg of the dried ethyl acetate extractables were dissolved in 1-ml 100% methanol and vortexed for 1 min. Subsequently, a 750 µl sample was removed from the stock solution and vortexed 1 min before being preparatively applied in a line at the origin on a silica gel preparative plate (20×20-cm, 500-µm thick) with a glass capillary tube obtained from Alltech Associates Inc., Deerfield, Ill. 60015. Before use, plates were kept in a desiccator. Plates were developed in a solvent mixture of chloroform:acetone:acetic acid (90:10:1) in a closed glass tank saturated with solvent vapors. The solvent was run up 65% of the plate area, and then the plate was allowed to air dry at room temperature. Resolved bands were first detected under a 254-nm UV light obtained from Mineral Light Lamp, UVSL-25; Ultra Violet Products, San Gabriel, Calif.

After a developed plate was thoroughly dried, a given (measured) strip(s) of silica gel was scraped off the plate with a razor blade, weighed and put into a 250-ml erlenmeyer flask. A known amount of 100% methanol in the ratio of 1-g silica gel/10-ml methanol (w/v) was added to the flask. Flasks were then covered with aluminum foil and set on an operating shaker for 12 hr. After the given time elapsed, the solution per flask was filtered through Whatman No. 2 filter paper and then rotoevaporated to reduce the volume of methanol to 1 ml. The 1 ml of extractables were placed in a preweighed vial, dried under a stream of nitrogen and the dry weight was determined. Extractables were redissolved in a known amount of 100% methanol and used in a feeding assay analogous to that described in Section IV.

IV. Dose-response test with ethyl acetate extractables from queen ash foliage

A dose-response study was conducted to determine the biologically active concentration range for the ethyl acetate extractables from green ash foliage. The following concentrations were employed: 0.025, 0.05, 0.10, 0.25, 0.5, 1.0, 2.0, 3.0, 5.0, 7.5, 10.0, 15.0 mg/ml (w/v), i.e., a known amount of dry ethyl acetate extractables was dissolved in 1 ml of 100% methanol. Two oak (host) leaf disks were presented per assay. Forty µl of an appropriate concentration of green ash extractables were presented as the treatment on the upper leaf surface on one of the two disks. An equal amount of 100% methanol was presented as the solvent control on the upper leaf surface on the other disk. Each extractables-containing vial was vortexed 1-min before a sample was removed and applied on a leaf disk. Two third-instar larvae were placed centrally between the treated and untreated (control) disks to initiate the assay.

Figure 3:
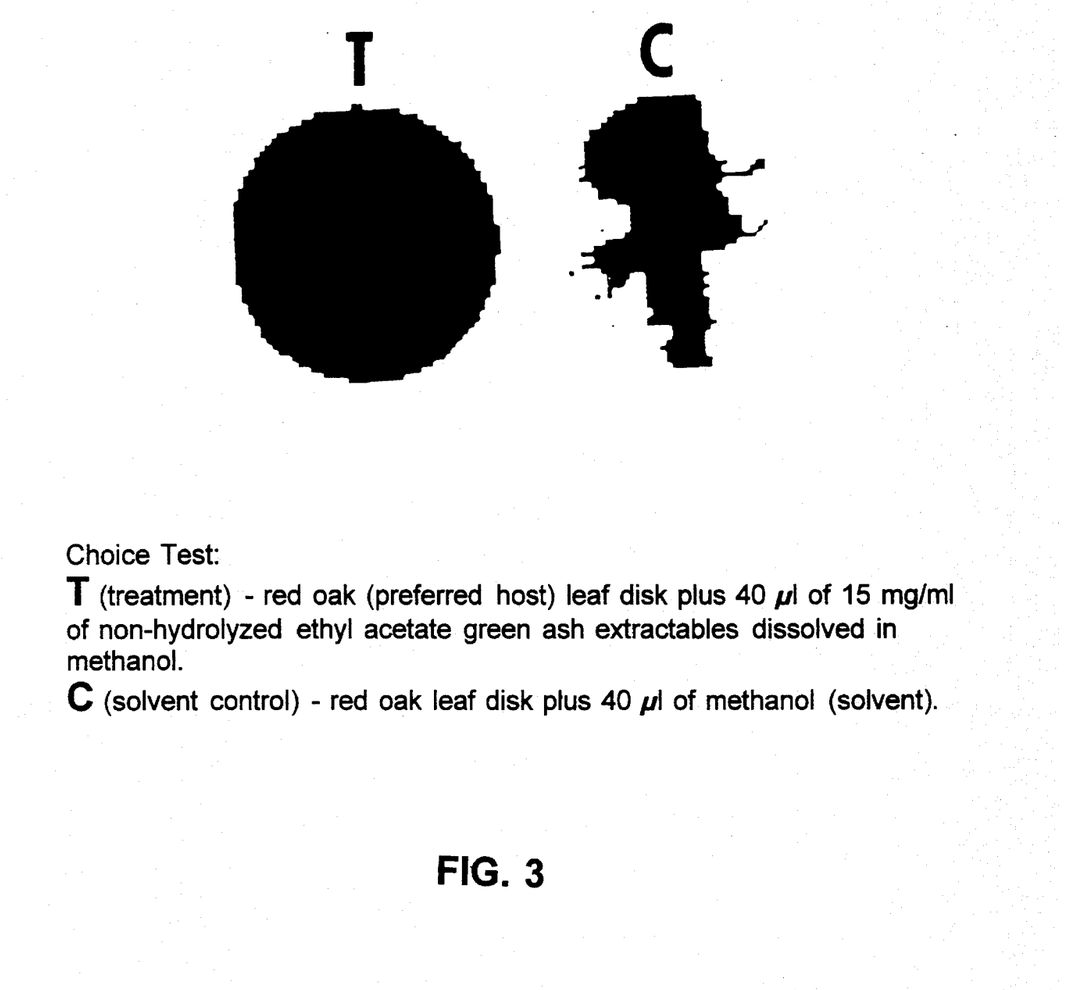
FIG. 3 is a graphical representation of choice feeding by gypsy moth larvae on an oak leaf treated either with 15 mg/ml of non-hydrolyzed ethyl acetate extractables, or with just methanol (solvent control).
Figure 4:
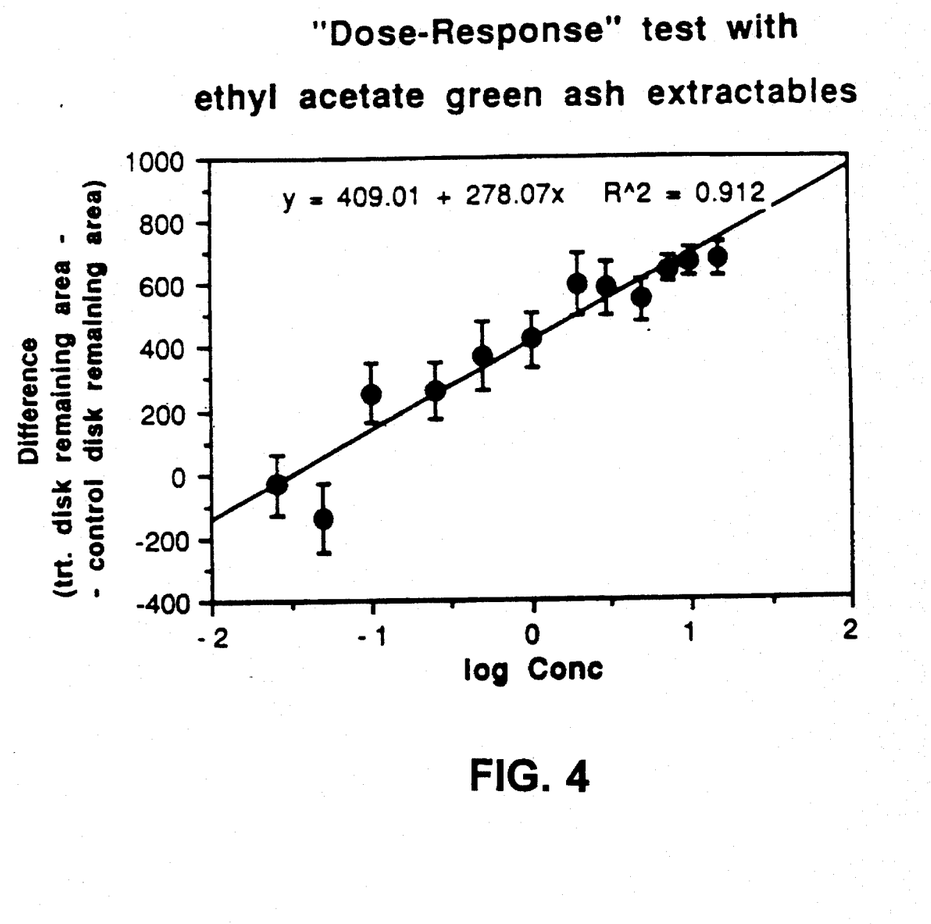
FIG. 4 is a graphical representation of a dose-response test of the gypsy moth-deterring activity of the substance of the present invention.

The results from the dose response tests are presented in FIGS. 3 and 4. These results clearly show that the green ash ethyl acetate extract is effective in a concentration of at least 0.1 mg/ml.

V. Acid hydrolysis of green ash ethyl acetate extractables

Acid hydrolysis, which may act to break glycosidic bonds (i.e., to separate aglycones from sugars in glycosides) was performed on a 50-mg sub-sample of the dried ethyl acetate extractables from each sample (i.e., jar). This sub-sample was hydrolyzed 1.5 hr in 2-molar hydrochloric acid at 105° C. The resultant hydrolyzed sub-sample was cooled, filtered through Whatman No. 2 paper and then extracted gradually with a total of 35 ml of chloroform under vacuum. Next, these extractables of the sub-sample were dried under a nitrogen stream, and their dry weight was determined.

The following concentrations were employed for the feeding bioassay: 0.10, 0.5, 2.0, 5.0 and 10.0 mg/ml (w/v), i.e., a known amount of dry chloroform extractables was dissolved in 1 ml of chloroform. The feeding bioassays comparing the activity of a hydrolyzed vs. a non-hydrolyzed fraction were conducted according to Section IV.

The results from the Section V tests are presented in FIG. 2. In FIG. 2, it evident from tests 3 and 4 compared to test 5, that acid hydrolysis of green ash ethyl acetate extractables destroys deterrent or inhibitory activity, and that the hydrolyzed extractables are excitatory to gypsy moth larval feeding at 5.0 and 10.0 mg/ml.

VI. Dose-response tests with aqueous extractables from green ash foliage

A dose-response study was conducted to determine the presence or absence of biologically active components in the residual aqueous extractables from green ash foliage, and the range of active concentrations if activity was detected. The following concentrations were employed: 0.10, 0.5, 2.0, 5.0 and 10.0 mg/ml (w/v), i.e., a known amount of dry aqueous extractables was dissolved in 1 ml of 80% methyl alcohol. The rest of this study was conducted in a manner analogous to that described in Section IV. A result from the Section VI tests is presented in FIG. 2. In FIG. 2, it is evident from test 6 that aqueous extractables from green ash foliage show no deterrent activity with gypsy moth larvae.

It is to be understood that the present invention is not confined to the particular construction and arrangement herein illustrated and described, but embraces such modified forms thereof as come within the scope of the following claims.

We claim:

1. A method of preparing a substance capable of deterring gypsy moths and larvae, the method comprising the steps of:
   (a) placing green ash foliage in contact with methanol to extract methanol-soluble compounds from the foliage,
   (b) filtering the methanol-soluble compounds from the foliage-methanol mixture;
   (c) concentrating the filtrate of methanol-soluble compounds; and
   (d) contacting the concentrated filtrate with ethyl acetate, thereby isolating ethyl acetate-soluble compounds from the concentrated filtrate of methanol-soluble compounds, such isolated compounds being capable of deterring gypsy moths and larvae.

2. The method of claim 1, further comprising the steps of:
   (e) drying the ethyl acetate extractables; and
   (f) dissolving the dried ethyl acetate extractables with methanol in a ratio of at least 0.1 mg dried extractables to 1 ml methanol.

3. A substance capable of deterring gypsy moths and larvae, the substance produced by the method comprising the steps of:
   (a) placing green ash foliage in contact with methanol to extract methanol-soluble compounds from the foliage;
   (b) filtering the methanol-soluble compounds from the foliage-methanol mixture;
   (c) concentrating the filtrate of methanol-soluble compounds; and
   (d) contacting the concentrated filtrate with ethyl acetate, thereby isolating ethyl acetate-soluble compounds from the concentrated filtrate of methanol-soluble compounds.

4. The substance of claim 3, the substance produced by the method further comprising the steps of:
   (e) drying the ethyl acetate extractables; and
   (f) dissolving the dried ethyl acetate extractables with methanol in a ratio of at least 0.1 mg dried extractables to 1 ml methanol.

5. A substance capable of deterring gypsy moths and larvae, the substance being represented by peaks having retention times of 13.67, 13.96, 14.19, 14.20, 14.46 and 14.82 minutes in the chromatogram set forth in FIG. 1.

6. The substance of claim 5, wherein the retention time-represented peaks comprise ethyl acetate-soluble compounds extracted from methanol-soluble compounds extracted from green ash foliage.

7. A method for deterring gypsy moths and larvae away from susceptible plants, the method comprising the steps of:
   (a) placing green ash foliage in contact with methanol to extract methanol-soluble compounds from the foliage;
   (b) filtering the foliage-methanol mixture;
   (c) concentrating the filtrate;
   (d) contacting the concentrated filtrate with ethyl acetate to extract ethyl acetate-soluble compounds from the concentrated filtrate; and
   (e) applying the ethyl acetate-extractables to plants susceptible to gypsy moths.

8. A method for deterring gypsy moths and larvae away from susceptible plants, the method comprising the step of applying to plants susceptible to gypsy moths a substance comprising ethyl acetate-soluble compounds extracted from methanol-soluble compounds extracted from green ash foliage.

* * * * *

UNITED STATES PATENT AND TRADEMARK OFFICE
CERTIFICATE OF CORRECTION

PATENT NO. : 5,614,196
DATED : March 25, 1997
INVENTOR(S) : Norris, Markovic It is certified that error appears in the above-identified patent and that said Letters Patent is hereby corrected as shown below:

In column 1, please insert the following text after the title:

-- STATEMENT REGARDING FEDERALLY SPONSORED RESEARCH

This invention was made with U.S. government support under USDA Hatch funds, Project #3419. The United States Government has certain rights in this invention. --

Signed and Sealed this

Twenty-third Day of December, 1997

*Attest:*

*Attesting Officer*

BRUCE LEHMAN
*Commissioner of Patents and Trademarks*